United States Patent [19]

Sakata et al.

[11] Patent Number: 4,481,808

[45] Date of Patent: Nov. 13, 1984

[54] METHOD AND APPARATUS FOR DETECTING THE CONCENTRATION OF A COMPONENT IN A SOLUTION

[75] Inventors: Jiro Sakata; Masana Hirai; Minoru Yamamoto, all of Nagoya, Japan

[73] Assignee: Kabushiki Kaisha Toyota Chuo Kenkyusho, Aichi, Japan

[21] Appl. No.: 234,069

[22] Filed: Feb. 12, 1981

[30] Foreign Application Priority Data

Feb. 20, 1980 [JP] Japan .................................. 55-20936

[51] Int. Cl.³ ............................................ G01N 13/00
[52] U.S. Cl. .................................. 73/61.1 R; 73/64.3
[58] Field of Search .................. 73/61 R, 61.1 R, 64.3

[56] References Cited

U.S. PATENT DOCUMENTS 3,455,147 7/1969 Peck et al. ............................ 73/64.3
3,957,648 5/1976 Roget et al. ...................... 210/321 B
4,137,756 2/1979 Cosack et al. ....................... 73/64.3

Primary Examiner—S. Clement Swisher
Attorney, Agent, or Firm—Blum Kaplan Fried Friedman Silberman & Beran

[57] ABSTRACT

Method and apparatus for determination of the concentration of a component in a solution, such as ethyl alcohol in gasohol, acetic acid in hexane-acetic acid solution, or the like. Such determination is made with ease and accuracy based on a rate of pressure change caused in a closed container due to mass transfer occurring between two liquids through porous material.

41 Claims, 13 Drawing Figures

F I G. 1
F I G. 2
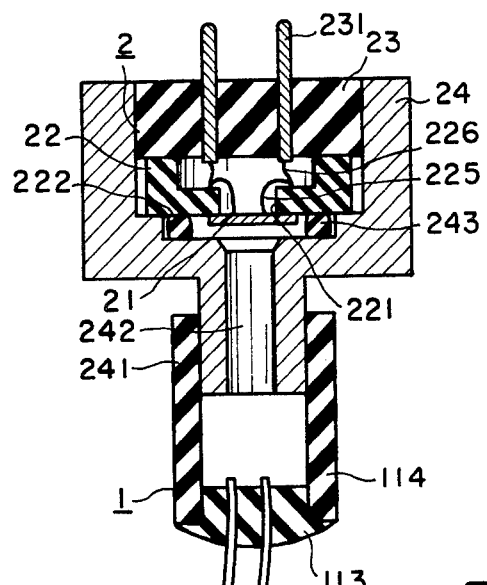
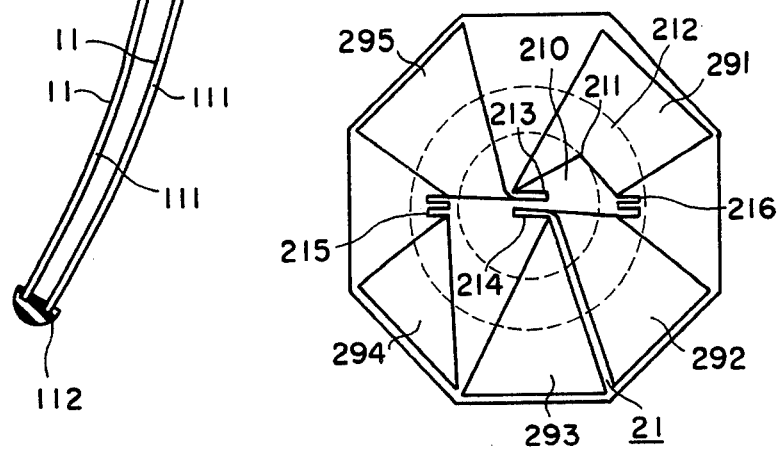

FIG. 3
FIG. 4
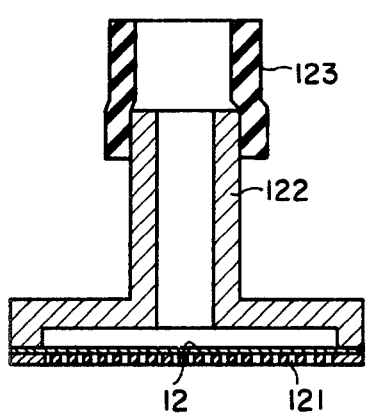
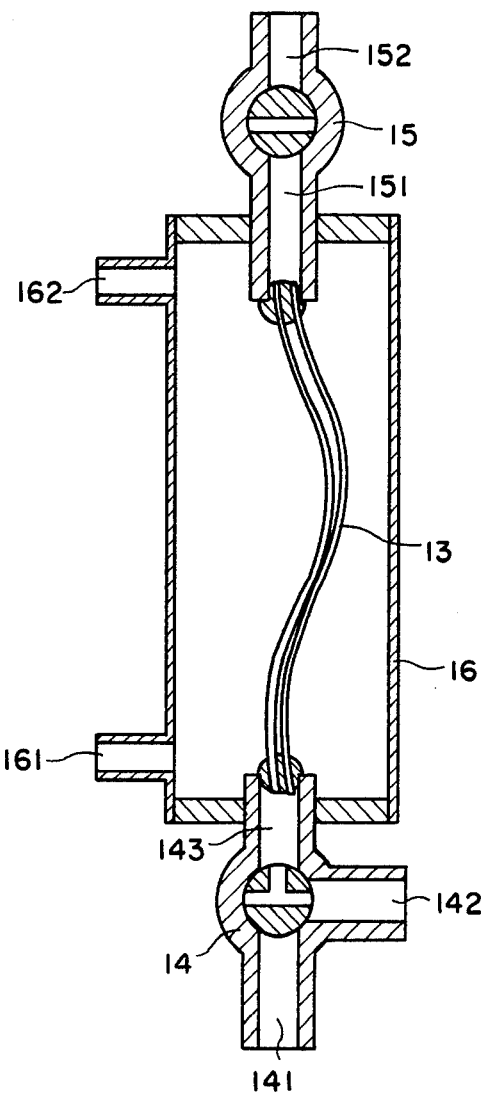

METHOD AND APPARATUS FOR DETECTING THE CONCENTRATION OF A COMPONENT IN A SOLUTION

BACKGROUND OF THE INVENTION

1. Field of the Invention

This invention relates to a method and apparatus for detecting the concentration of a component in a solution by utilizing a rate of mass transfer occurring between two liquids through a partition formed by porous material having fine through pores.

2. Description of the Prior Art

There has been a continual requirement for a method and apparatus which facilitate determination of the concentration of a specific component in a solution. Particularly in view of the recent attempt to realize the use as an automobile fuel of gasohol obtained by mixing ethyl alcohol into gasoline, it is strongly desired to develop a method and apparatus which facilitate determination of the concentration of a component in a solution, such as ethyl alcohol in gasohol.

SUMMARY OF THE INVENTION

Accordingly, one object of the present invention is to provide a method and apparatus for determination of the concentration of a component in a solution with ease and high accuracy, based on a rate of pressure change caused by mass transfer occurring between two liquids through porous material.

Another object of the invention is to provide a method and apparatus for easily detecting the concentration of ethyl alcohol in gasohol with an accuracy of about ±1%.

Still another object of the invention is to provide a method and apparatus for use in the nearly continuous determination of the concentrations of components in a variety of kinds of liquids.

The inventors of this invention have discovered that if gasoline containing a certain amount of ethyl alcohol is placed in contact with one surface of a partition formed by porous material having fine through pores, and a closed space defined by the other surface of the partition is filled with water, ethyl alcohol passes through the through pores of the partition and is dissolved in water, resulting in an increase of the pressure in the closed space.

After examining in detail the relation between an increase of the pressure per unit time, or a rate of its increase and the concentration of ethyl alcohol in gasohol, the inventors have discovered the presence of a linear relationship therebetween, and arrived at the present invention. Accordingly, if the relationship between an increase of pressure per unit time, or a rate of its increase and the concentration of ethyl alcohol in gasohol is available, it is possible to determine the unknown concentration of ethyl alcohol in gasohol by obtaining an increase of pressure per unit time, or a rate of its increase.

According to this method, it is possible to determine very easily and accurately with an accuracy of about ±1% the concentration of ethyl alcohol in gasohol which has heretofore been very difficult to determine. This invention is based on such discovery.

The method of this invention, is thus, characterized by placing one of a first liquid and a second liquid containing a component soluble in the first liquid in a closed container having a partition formed at least partially by porous material having fine through pores, positioning the other of the first and second liquids outwardly of, and in contact with the partition formed by the porous material, detecting as a rate of pressure change in the closed container a rate of the mass transfer occurring between the first and second liquids through the partition of the porous material, and determining the concentration of the component from the rate of pressure change.

The apparatus of this invention is an apparatus for detecting the concentration of a component in a solution by placing a first liquid on one side of a partition formed by porous material having fine through pores, and a second liquid containing a component soluble in the first liquid on the other side of said partition, and determining the concentration of the component in the second liquid from a rate of the mass transfer occurring between the first and second liquids through the partition of the porous material, and characterized by comprising a closed container having at least a portion of its partition formed by the porous material, and a pressure detecting means for detecting the rate of the mass transfer occurring through the partition of the closed container as a rate of pressure change in the closed container.

BRIEF DESCRIPTION OF THE DRAWINGS

Various other objects, features and advantages of the present invention will be more fully appreciated as the same becomes better understood from the following detailed description when considered in connection with the accompanying drawings wherein:

FIG. 1 is a cross-sectional view of the apparatus embodying this invention, and having a partition formed by hollow fibers;

FIG. 2 is a view showing the arrangement of strain gauge elements on a diaphragm for a pressure detecting device in the apparatus shown in FIG. 1;

FIG. 3 is a cross-sectional view of the partition formed by using a sheet;

FIG. 4 is a cross-sectional view of another apparatus embodying this invention;

FIG. 9 shows a working curve obtained from the measurements by the apparatus of this invention shown in FIG. 1 for determining an acetic acid concentration in a mixed hexane-acetic acid solution;

FIG. 10 shows a working curve obtained by using the apparatus of FIG. 4 for determining an ethyl alcohol concentration in gasohol;

FIG. 11 shows a working curve obtained by using the apparatus of FIG. 4 for determining an ethyl alcohol concentration in a mixed solution containing water and ethyl alcohol;

FIG. 12 shows a working curve obtained by using the apparatus of FIG. 4 for determining an ethyl alcohol concentration in a mixed hexane-ethyl alcohol solution; and FIG. 13 shows a working curve obtained by using the apparatus of FIG. 4 for determining an acetone concentration in a mixed ethylene glycol-acetone solution.

DETAILED DESCRIPTION

Figure 5:
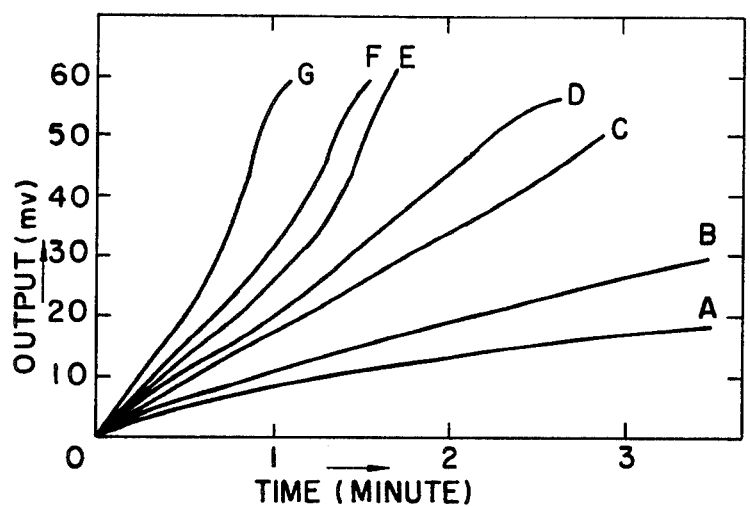
FIG. 5 is a graph showing the relationship between the time and the output for each of different ethyl alcohol concentrations in gasohol as examined by the apparatus shown in FIG. 1.

The porous material having fine through pores in the present invention is a substance having a multiplicity of holes extending from one surface of the partition to the other, and which holes have as small a cross-sectional area as possible for a given circumferential length.

The porous material must be of the type which is not dissolved when contacted by the liquid to be tested. It is also not desirable to use the material which is likely to swell or be deformed heavily upon pressure increase or when contacted with the liquid, since the pressure increase caused by the dissolution of the component to be detected fails to be reflected precisely, rendering the measurement inaccurate. The porous material must not be of the type in which the liquid easily leaks out from the closed space through its holes upon pressure increase therein. Such leakage, if any, results in a reduction in the amount of pressure change, and a lowered accuracy of the measurement. In order to avoid easy leakage of the liquid through its holes, it is desirable for the porous material to be of the hydrophobictype. More specifically, as it is, for example, possible that when the closed space is filled with water, the dissolution in the aqueous phase of the component to be detected forms an aqueous solution thereof having a lower surface tension, resulting in easy leakage of water, it is desirable to use the porous material having a critical surface tension which is lower than the surface tension of the aqueous solution so formed, in order to avoid leakage of water through its holes. Specific examples of the porous material include polypropylene, polytetrafluoroethylene (Teflon) and polycarbonate. Even if suitable porous material is employed, however, it is possible that there may be only too small a pressure increase, or no pressure increase at all in the closed space, if its holes are too large, or sufficiently small but the material is so small in thickness. The propriety of a particular kind of porous material for use in the measurement according to this invention is difficult to discuss in general terms, since it involves a lot of complicated factors such as material, pore size and shape, and thickness. There is generally no limitation to the shape of the pores; they may, for example, be circular, elliptical or linear.

In order to avoid free leakage of the liquid through the pores, it is desirable that they are not larger than several tens of micro-meters in diameter if they are circular, or in width if they are linear. It is, however, desirable for their diameter or width not to be smaller than several tens of angstroms, since too small pores fail to respond quickly for measurement. The thickness of the partition is preferably from several to several hundreds of micro-meters, since it fails to respond quickly enough if too thick, while it is low in mechanical strength, or is likely to be deformed easily upon pressure increase if it is too thin. These values are, however, shown merely to provide a general standard, and there is every likelihood that any material deviating from the aforesaid dimensional ranges may be very satisfactory for use in the method of this invention if it is suitable in other properties. Some porous material that is hydrophilic may be useful if its pores satisfy the requirements, or may be applicable if its surface is made hydrophobic by suitable treatment.

The porous material may be in the shape of thin tubes or a flat membrane, and both of these shapes can be used for the method of this invention. If the porous material in the shape of a flat membrane is used, however, it is necessary to pay careful condiseration in the design of the apparatus to the fact that a membrane is likely to be deformed easily upon pressure increase or by contact with the liquid into a shape which may have an adverse effect on the accuracy of the measurement. The porous material which can be effectively used may be a polycarbonate film having a thickness of about 5 micrometers, and provided with cylindrical through holes each having a substantially ciruclar cross section and a diameter of 0.01 to 0.1 micro-meter, or a polypropylene film provided with curved through holes each having a linear cross section and measuring approximately from 0.01 by 0.1 micro-meter to 2 by 10 micro-meters, a film of a fluorine-contained resin, or a hollow fiber formed from any such film.

The closed container used for this invention has at least a portion of its partition formed by the aforesaid porous material. The closed container may be extremely small, and is large enough if it can define a closed space having a volume of about 0.05 cm$^3$. The closed container serves as a pressure holding vessel, and must be able to withstand a pressure differential of at least about 0.1 atmosphere. The apparatus is likely to be slower in response with an increase in the size of the closed container, with a reduction in the surface area of the partition formed by the porous material, or with a decrease in the total cross-sectional area of the through holes, though it permits measurement.

Although it is theoretically possible to employ any combination of the first and second liquids, it is desirable to choose a combination of liquids forming a stable interface therebetween, such as water and oil. A combination of liquids which do not easily form a stable interface therebetween presents a number of problems, such as the necessity of finishing the measurement in a short time, and the low accuracy of measurement. It is qualitatively desirable to employ a combination of a hydrophilic liquid and a hydrophobic liquid. Typical examples of the hydrophilic liquid include water, alcohols, and organic and inorganic acids, and typical examples of the hydrophobic liquid are liquids of the hydrocarbon series, such as pentane, hexane, toluene and gasoline, and organic solvents such as carbon tetrachloride. If a combination consists of water as a hydrophilic liquid, and a hydrocarbon or an organic solvent like carbon tetrachloride as a hydrophobic liquid, it is possible to determine easily and accurately the concentration of ethyl alcohol, methyl alcohol, acetic acid, or the like in the hydrophobic liquid.

It is desirable for the porous material to be of the hydrophobic type in relation to the first and second liquids. When the partition of the porous material is interposed between the first and second liquids, the hydrophobic liquid or a component thereof moves into the hydrophilic liquid through the holes extending through the porous material. Accordingly, the hydrophilic liquid shows a relative increase in volume. Insofar as the hydrophilic liquid is confined in the closed container, its increase in volume can be detected as an increase of pressure in the closed container. If it is the hydrophobic liquid that is confined in the closed container, the movement of the liquid can be detected as a decrease of the pressure in the closed container. If the liquid in the closed container and the liquid in its exterior are brought into contact with each other through the porous partition having fine through holes, it is definitely true that the liquid movement can be detected as a pressure change in the closed container. The action by which the pressure differential created between the interior and exterior of the closed container is maintained has, however, not been clarified as yet.

The pressure increase recognized by the method of this invention as hereinabove described is usually as much as about 0.1 atmosphere. As it is actually necessary to calculate an increase of pressure per unit time, or a rate of its increase from a change of pressure only in the amount of several tens of Torr during the initial period of dissolution, it is advantageously possible to use various strain pressure gauges capable of reading pressures above several Torr, including existing semiconductor pressure transducing elements. According to the method of this invention, however, it is important to determine very small changes in volume by pressure in view of the fact that a liquid is an incompressible fluid, and therefore, it is not advisable to use any pressure gauge of the type in which an increase in pressure is substantially damped by a layer containing a large quantity of gas.

Actually, however, there are often various restrictions which make it difficult to fill the closed space with a liquid completely, and make it unavoidable to leave a layer of some gas therein. The presence of such a gaseous layer does not present any appreciable problem, if an increase in the volume of the liquid caused by dissolution of the substance to be detected is sufficiently large to overcome the damping action by the compression of the gaseous layer. It is, however, necessary to maintain a constant amount of gas in the gaseous layer at all times, since any change in the amount of gas necessarily leads to changes in the magnitude of its damping action and in an increase of pressure. If careful attention is paid to this aspect, it is possible to perform measurement with a high degree of reproducibility and accuracy irrespective of the presence of any such gaseous layer in the closed space, unless the gaseous layer is extremely greater than the liquid layer, resulting in a very small increase in pressure. Description will now be made of the apparatus of this invention for detecting the concentration of a component in a solution. Referring first to FIG. 1, there is shown in cross section a typical apparatus having a closed container defined by thin tubes. The apparatus comprises a porous partition formed by a pair of hollow fibers 11 of porous polypropylene having an outside diameter of 250 micro-meters, an inside diameter of 200 micro-meters and a length of about 4 cm. The hollow fibers 11 have internal spaces 111 connected with a pressure receiving space 242 in a pressure detecting device 2 by a synthetic resin connecting tube 114. One end of each of the two hollow fibers 11 is secured to a synthetic resin adhesive 112, and closed by it. The other end of each hollow fiber 11 extends into the connecting tube 114, and is joined to one end of the connecting tube 114 in a gas-tight fashion by an adhesive 113. The other end of each hollow fiber 11 is not closed, but opens in the connecting tube 114. The pressure detecting device 2 consists mainly of a pressure receiving diaphragm 21 made of silicon single crystal, a member 22 supporting the diaphragm 21, a cover 23 to which connector pins 231 are secured, and a casing 24. The disphragm 21 is composed of N-silicon single crystal, and in a position corresponding to the ciruclar open end of the supporting member 22, and in appropriate locations in the vicinity 210 of its axis and the outer peripheral area 212 of a strain reversal boundary 211, P-type strain sensitive portions 213, 214, 215 and 216 each having a small area defined by an extremely large length relative to its width are formed in channel-like and arcuate shapes by diffusion of boron as an impurity according to known planar technique, and joined with the diaphragm 21 integrally and in an electrically insulating fashion. Electrodes 291 to 295 are formed by evaporation of aluminum on outer edge portions in the peripheral area of the diaphragm for highly conductive connection of gold lead wires. After a gold lead wire 225 has been connected to each electrode, the diaphragm is secured in an electrically insulating fashion to the open end 221 of the cylindrical supporting member 22 having a shoulder 222 in its inner periphery, and formed from ceramics having a coefficient of thermal expansion close to that of silicon, e.g., cordierite. After the gold lead wires 225 are connected to the electrodes provided in the shoulder of the base body, each lead wire is electrically connected by a thicker lead wire 226 to one end of a connector pin 231 in the electrically insulative cover 23 provided in the other open end of the base body. The silicon diaphragm 21 and the supporting member 22, the supporting member 22 and the cover 23, and the cover 23 and the connector pins 231 are joined respectively with each other by an epoxy resin adhesive.

The casing 24 is made of a metal, and accommodates the supporting member 22 therein. The casing 24 is provided at its bottom with a projection 241 engaged in the connecting tube, and having a through axial bore defining the pressure receiving space 242. The casing 24 and the supporting member 22 are sealed against each other in a gastight fashion by a rubber ring 243, and the casing 24 and the cover 23 are joined with each other in a gastight fashion by an adhesive. The projection 241 of the casing 24 is received in the other end of the connecting tube 114, and the gastightness therebetween is maintained by the elasticity of the connecting tube 114. The projection 241 and the connecting tube 114 are removable from each other, as they are retained together by the elasticity of the connecting tube 114.

According to the apparatus of this invention as hereinabove described, its closed container 1 is formed by the hollow fibers 11, the connecting tube 114, and the casing 24; the supporting member 22, the rubber ring 243 and the diaphragm 21 in the pressure detecting device 2. The hollow fibers of porous polypropylene are used as the porous material. The hollow fibers have linear pores formed among polypropylene crystals, and measuring about 0.05 by 0.3 micro-meter.

When the apparatus is used for detecting the concentration of a component in a solution, the projection 241 of the casing 24 is detached from the connecting tube 114, and a particular liquid, e.g., water, is charged into the hollow fibers 11 and the pressure receiving space 242 in the casing 24. The projection 241 is, then, inserted into the connecting tube 114 again, whereby the closed space in the apparatus is filled with water. Then, the hollow fibers 11 are immersed in the liquid to be tested, e.g., gasohol. This procedure allows alcohol in the gasohol to pass through the walls of the hollow fibers 11 into the closed space to thereby create an increased pressure therein. This pressure increase is detected by the pressure detecting device 2, and the concentration of alcohol in the gasohol is obtained from the rate of such pressure increase.

Although the embodiment as hereinabove described employs the pressure detecting device of the type in which the pressure sentitive diaphragm 21 per se is used as a semiconductor strain gauge, it does not limit the pressure detecting device, but it is equally possible to use various other types of pressure measuring instruments.

Attention is now directed to FIG. 3 showing a partition formed by a sheet of porous material instead of the hollow fibers 11 as shown in FIG. 1. The partition comprises a porous sheet 12, a net of backing material 121 reinforcing the porous sheet 12, a base member 122 in the shape of a cup having an open bottom closed by the backing material 121 and defining an internal space therein, and a synthetic resin connecting tube 123 for connection to a pressure detecting device not shown. The combination of the partition shown in FIG. 3 with the pressure detecting device 2 shown in FIG. 1 constitutes an apparatus of this invention for detecting the concentration of a component in a solution. This type of apparatus requires the backing material 121 for supporting the pressure acting on the porous sheet 12, as it cannot be borne by the porous sheet 12 alone. The backing material 121 can, however, be eliminated if the porous sheet 12 is sufficiently rigid and strong.

Reference will now be made to FIG. 4 showing an apparatus which facilitates the exchange of a liquid in the closed container. This apparatus is constituted mainly by a three-way cock 14 having a passage 141 defining an inlet for liquid, a passage 142 connected to a pressure detecting device not shown, and a passage 143 connected to a porous partition 13, a two-way cock 15 having a passage 151 connected to the porous partition 13 and a passage 152 defining a liquid outlet, and the porous partition 13 disposed between the three-way cock 14 and the two-way cock 15. The porous partition 13 is formed by hollow fibers having opposite open ends which open in the passage 143 of the three-way cock 14 and the passage 151 of the two-way cock 15, respectively, and is joined to the three-way and two-way cocks 14 and 15 in a gastight fashion by an adhesive. The apparatus includes a container 16 formed around the porous partition 13 for receiving the liquid to be tested therein. The container 16 has an inlet 161 for the liquid to be tested at its bottom, and an outlet for the liquid at its top. In operation, after the passage 142 is connected to the pressure detecting device, the three-way cock 14 is operated for connection of its passages 141 and 143, and the two-way cock 15 is opened, so that water, for example, may be introduced through the passage 141 to fill the space between the two cocks. Then, the two cocks are closed between the passages 141 and 152 as shown in FIG. 4. The liquid to be tested, e.g., gasohol, is introduced into the container 16, so that the alcohol in the gasohol may flow through the porous partition 13 into the closed container. The rate of such flow of alcohol into the closed container is detected by the pressure detecting device to determine the concentration of the alcohol in the gasohol.

As the operation of the cocks makes it possible to exchange the liquid (water) in the closed container relatively easily, the apparatus is advantageous for use in the determination of the concentrations of components in a variety of kinds of liquids, or in the nearly continuous determination of the concentrations of components in liquids.

The invention will now be described in further detail with reference to examples of measurement. TABLE 1 shows the type and physical properties of the porous partitions used for the measurement.

Example of Measurement 1

The concentration of alcohol (ethyl alcohol) in gasohol was detected by an apparatus which was of the substantially equal construction to that shown in FIG. 1. The porous partition was formed by two polypropylene fiber (PPF) tubes each having a length of 4 cm. The closed space had a volume of about 0.06 cm$^3$, and the porous partition had a surface area of about 0.6 cm$^2$. A semiconductor pressure transducer which was similar to that shown in FIG. 1 was used as a pressure detecting device. The closed space was filled with water, and new water was used for each measurement.

TABLE 1

| Type of porous partition | Material | Shape | Thickness (micrometers) | Pore shape | Pore size (Å) | Others |
|---|---|---|---|---|---|---|
| PP | Polypropylene | Flat membrane | 25 | Rectangular | 200 × 2,000 | |
| PC-1 | Polycarbonate | Flat membrane | 5 | Circular | 1,000 dia. | |
| PC-2 | Polycarbonate | Flat membrane | 5 | Circular | 500 dia. | |
| PC-3 | Polycarbonate | Flat membrane | 5 | Circular | 300 dia. | |
| TFE | Polytetrafluoroethylene | Flat membrane | 60 | Rectangular | 2,000 × 50,000 | |
| PPF | Polypropylene | Thin tube | 25 | Rectangular | 500 × 3,000 | 250 micrometers (outer dia.) |

Figure 6:
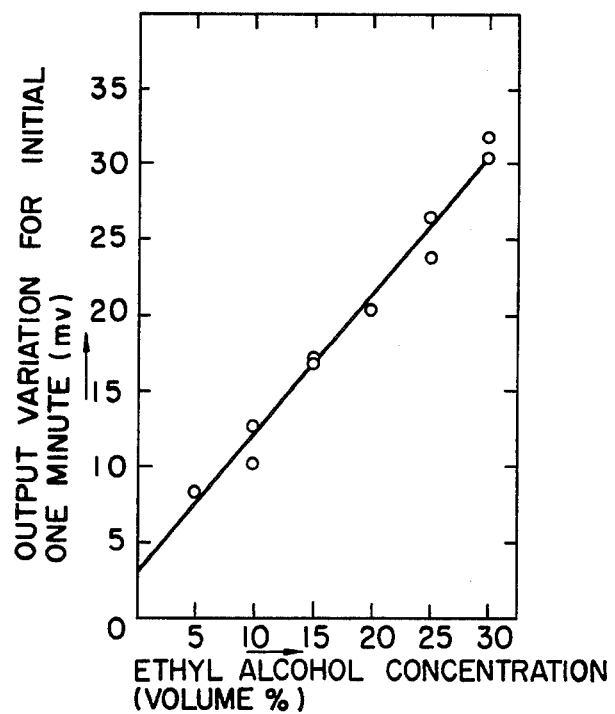
FIG. 6 shows a working curve obtained from the test results of FIG. 5 for determining an ethyl alcohol concentration in gasohol.

FIG. 5 shows the relation between the time for which the porous partition was immersed in seven kinds of gasohol having different alcohol concentrations, and the output voltage as measured. In FIG. 5, symbols A to G indicate the results of measurement for gasohols having alcohol concentrations of 5% (by volume throughout this specification), 10%, 15%, 20%, 25%, 30% and 40%, respectively. It is noted from this figure that the output shows a substantially linear increase for about one minute after the measurement is started. The output variations which had occurred during the period of one minute following the initiation of the measurement were obtained in relation to the alcohol concentration based on the data of FIG. 5, and are shown in FIG. 6. It is noted from FIG. 6 that there is a linear relationship between the alcohol concentration and the output variation for the initial period of one minute. The curve 5 shown in FIG. 6 can be used as a working curve for determining the unknown concentration of alcohol in gasohol. The working curve differs with the type of the porous partition employed, its surface area, the size of the closed space defined therein, and the like, and must, therefore, be obtained for each apparatus.

Example of Measurement 2

Figure 7:
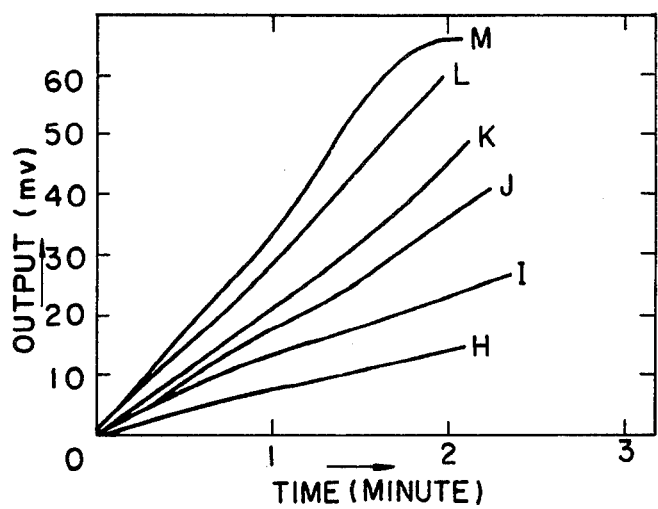
FIG. 7 is a graph showing the relationship between the time and the output for each of different ethyl alcohol concentrations in mixed hexane-ethyl alcohol solutions as examined by the apparatus shown in FIG. 1.
Figure 8:
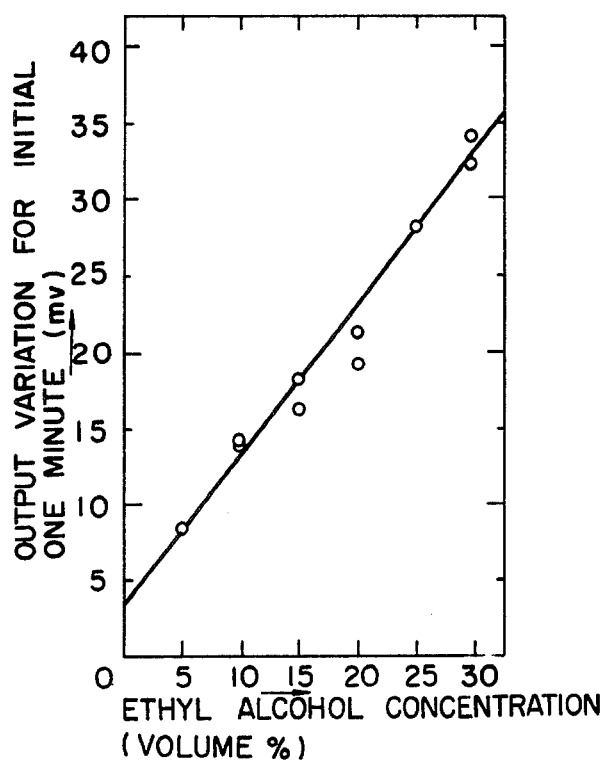
FIG. 8 shows a working curve obtained from the test results of FIG. 7 for determining an ethyl alcohol concentration in a mixed hexane-ethyl alcohol solution.

The concentration of ethyl alcohol in a mixed solution containing hexane and ethyl alcohol by the apparatus and method employed in Example of Measurement 1. FIG. 7 shows the relation between the immersion time and the output voltage for each of six kinds of mixed solutions having different ethyl alcohol concentrations. Symbols H to M indicate the results of measurement for the mixed hexaneethyl alcohol solutions having ethyl alcohol concentrations of 5%, 10%, 15%, 20%, 25% and 30%, respectively. The output variations which had occurred during the period of one minute following the initiation of the measurement were examined in relation to the ethyl alcohol concentration based on the data of FIG. 7, and are shown in FIG. 8. The straight line shown in FIG. 8 can be used as a working curve for water and mixed solutions containing hexane and ethyl alcohol.

Example of Measurement 3

The same apparatus and method as employed in Example of Measurement 1 were used for testing mixed solutions containing hexane and acetic acid. The working curve thereby obtained for water and mixed solutions containing hexane and acetic acid is shown in FIG. 9.

Example of Measurement 4

The concentration of ethyl alcohol in mixed solutions containing hexane and ethyl alcohol was measured by an apparatus which was substantially equal to the combination of the partition shown in FIG. 3 with the pressure detecting device in FIG. 1. The porous sheet comprised a disc of polypropylene having a diameter of 1 cm. The closed space had a volume of about 0.1 $cm^3$, and the porous sheet had an effective surface area of about 0.2 $cm^2$. The closed space was filled with water, and new water was used for each measurement.

TABLE 2 shows the output variations observed during the period of one minute following the initiation of the measurement for each of the mixed hexane-ethyl alcohol solutions having an ethyl alcohol concentration of 0%, 15% and 30%, respectively. It is noted from this table that there is a relationship of substantially direct proportion between the alcohol concentration and the output variation for the initial period of one minute. Accordingly, this relationship can be utilized for determining the unknown concentration of alcohol in such mixed solutions.

TABLE 2

| | Membrane | Alcohol concentration | | |
|---|---|---|---|---|
| | | 0% | 15% | 30% |
| | | Output variation for initial one-minute period (mV) | | |
| Example 4 | PP | 0 | 1.4 | 3.0 |
| Example 5 | PC-1 | 0 | 4.2 | 9.0 |
| Example 6 | PC-2 | 0 | 11.0 | 23.0 |
| Example 7 | PC-3 | 0 | 5.5 | 12.0 |
| Example 8 | TFE | 0 | 8.0 | 14.5 |

Examples of Measurement 5 to 8

The procedures of Example 4 were repeated for a further series of measurements, except that the porous sheet was formed from PC-1 (Example 5—polycarbonate), PC-2 (Example 6—polycarbonate), PC-3 (Example 7—polycarbonate) and TFE (Example 8—polytetrafluoroethylene). The results are shown in TABLE 2. A substantially directly proportional relationship was observed between the alcohol concentration and the output variation for the initial period of one minute, whatever material the porous sheet was made of.

Example of Measurement 9

The concentration of ethyl alcohol in gasohol was detected by an apparatus which was substantially of the same construction as shown in FIG. 4. The porous partition was formed by two thin polypropylene fiber (PPF) tubes each having a length of 5 cm. The closed space had a volume of about 0.15 $cm^3$, and the porous partition had a surface area of about 0.8 $cm^2$. The pressure detecting device was a semiconductor pressure transducer of the same type as shown in FIG. 1. The closed space was filled with water, and new water was used for each measurement by the cock operation as hereinbefore described. Measurements were conducted five times for each of gasohol solutions having alcohol concentrations of 0%, 5%, 10%, 15%, 20%, 25% and 30%, respectively. The relationship thereby obtained between the output variation which occurred during the period of one minute following the initiation of the measurement, and the alcohol concentration is shown in FIG. 10. In FIG. 10, the small circles indicate the average values obtained from the five times of measurement, and the symbols I indicate the range of the different values as actually obtained by the measurement. It is, thus, noted that the values obtained by a number of times of measurement show only a very small difference from one another if the apparatus as shown in FIG. 4 is used. The curve obtained by joining the average values can be used as a working curve for very accurate determination of the unknown concentration of alcohol in gasohol.

Example of Measurement 10

Mixed solutions containing water and ethyl alcohol were examined by the same apparatus and method as employed in Example 9. The working curve thereby obtained with respect to water and mixed solutions containing water and ethyl alcohol is shown in FIG. 11.

Example of Measurement 11

Mixed hexane-ethyl alcohol solutions were examined by using the same apparatus as employed in Example 9, except that the closed space was filled with hexane. A drop in the pressure of the closed space was observed. The relationship thereby obtained between the output variation for the period of one minute following the initiation of the measurement and the alcohol concentration is shown in FIG. 12. It is noted that even in the event a pressure drop occurs in the closed space, there exists a linear relationship between the output variation for the initial period of one minute and the alcohol concentration, which can be used for establishing a working curve.

Example of Measurement 12

Mixed ethylene glycol-acetone solutions were examined by using the same apparatus as employed in Example 9, except that the closed space was filled with hexane. The working curve thereby obtained with respect to hexane and mixed ethylene glycol-acetone solutions is shown in FIG. 13.

Having now fully described this invention, it will be apparent to one of ordinary skill in the art that many changes and modifications can be made without departing from the spirit or scope of the invention set forth herein.

What is claimed is:

1. A method for detecting the concentration of a component in a solution, comprising the steps of
    placing one of a first liquid and a second liquid containing a component soluble in said first liquid in a closed container having a partition formed at least partially by porous material having small through pores and having a critical surface tension which is lower than a surface tension of said first liquid when said component in said second liquid is dissolved therein,
    positioning the other of said first and second liquids outwardly of, and in contact with said partition formed by said porous material,
    detecting as a rate of pressure change in said closed container a rate of the mass transfer occurring between said first and second liquids through said partition of said porous material, and
    determining the concentration of said component from said rate of pressure change.

2. A method for detecting the concentration of a component in a solution, comprising the steps of
    placing one of a first liquid and a second liquid containing a component soluble in said first liquid in a closed container having a partition formed at least partially by porous material in the shape of thin tubes having small through pores,
    positioning the other of said first and second liquids outwardly of, and in contact with said partition formed by said porous material,
    detecting as a rate of pressure change in said closed container a rate of the mass transfer occurring between said first and second liquids through said partition of said porous material, and
    determining the concentration of said component from said rate of pressure change.

3. A method according to claim 2, wherein said thin tubes are hollow fibers.

4. A method according to claim 1, wherein said porous material is in the shape of a flat membrane.

5. A method according to claim 4, which further comprises backing material for reinforcing said flat membrane.

6. A method according to claim 1, wherein said through pores of said porous material is of a shape selected from the group consisting of circular, elliptical and linear shapes.

7. A method according to claim 2, wherein the size of said through pores of said porous material is from several tens of angstroms to several tens of micro-meters.

8. A method according to claim 7, wherein the thickness of said partition formed by said porous material is from several to several hundreds of micro-meters.

9. A method according to claim 2, wherein said porous material is hydrophobic.

10. A method according to claim 9, wherein said porous material is selected from the group consisting of polypropylene, polytetrafluoroethylene and polycarbonate.

11. A method according to claim 2, wherein said first and second liquids form a stable interface therebetween.

12. A method according to claim 11, wherein said first liquid is hydrophilic and said second liquid is hydrophobic.

13. A method according to claim 12, wherein said first liquid is selected from the group consisting of water, alcohols, and organic and inorganic acids.

14. A method according to claim 13, wherein said second liquid is a hydrocarbon.

15. An apparatus for detecting the concentration of a component in a solution comprising
    a closed container for enclosing one of a first liquid and a second liquid containing a component soluble in said first liquid, having a partition formed at least partially by porous material, said porous material having small through pores and having a critical surface tension which is lower than a surface tension of said first liquid when said component in said second liquid is dissolved therein, and
    a pressure detecting means for detecting the rate of the mass transfer occurring through said partition of said closed container as a rate of pressure change in said closed container.

16. An apparatus for detecting the concentration of a component in a solution by placing a first liquid on one side of a partition formed by porous material in the shape of thin tubes having small through pores, and a second liquid containing a component soluble in said first liquid on the other side of said partition, and determining the concentration of said component in said second liquid from a rate of the mass transfer occurring between said first and second liquids through said partition of said porous material, comprising
    a closed container having a least a portion of its partition formed by said porous material, and
    a pressure detecting means for detecting the rate of the mass transfer occurring through said partition of said closed container as a rate of pressure change in said closed container.

17. An apparatus according to claim 16, wherein said thin tubes are hollow fibers.

18. An apparatus according to claim 15, wherein said porous material is in the shape of a flat membrane.

19. An apparatus according to claim 18, which further comprises backing material for reinforcing said flat membrane.

20. An apparatus according to claim 15, wherein said through pores of said porous material is of a shape selected from the group consisting of circular, elliptical and linear shapes.

21. An apparatus according to claim 16, wherein the size of said through pores of said porous material is from several tens of angstroms to several tens of micrometers.

22. An apparatus according to claim 21, wherein the thickness of said partition formed by said porous material is from several to several hundreds of micro-meters.

23. An apparatus according to claim 16, wherein said porous material is hydrophobic.

24. An apparatus according to claim 23, wherein said porous material is selected from the group consisting of polypropylene, polytetrafluoroethylene and polycarbonate.

25. An apparatus according to claim 16, which further comprises a three-way inlet cock having a first passage for introducing one of said first and second liquids, a second passage connected to said pressure detecting device and a third passage connected to one end of said porous material, and a two-way outlet cock having a first passage connected to the other end of said porous material and a second passage for removing one of said first and second liquids, thereby facilitating the exchange of liquid.

26. An apparatus according to claim 16, which further comprises a vessel having an inlet and an outlet, formed around said porous material for receiving the other of said first and second liquids.

27. A method according to claim 1, wherein said first liquid is water and said second liquid is a mixture of gasoline and one of ethyl alcohol and methyl alcohol.

28. A method for detecting the concentration of a component in a solution, comprising the steps of placing one of a first liquid and a second liquid containing a component soluble in said first liquid in a closed container having a partition formed at least partially by porous material having small through pores wherein the side of said through pores of said porous material is from several tens of angstroms to several tens of micro-meters, positioning the other of said first and second liquids outwardly of, and in contact with said partition formed by said porous material, detecting as a rate of pressure change in said closed container a rate of the mass transfer occurring between said first and second liquids through said partition of said porous material, and determining the concentration of said component from said rate of pressure change.

29. A method according to claim 28, wherein the size of said through pores of said porous material is from several tens of angstroms to several tens of micrometers.

30. A method according to claim 1, weherin said porous material is hydrophobic.

31. A method according to claim 30, wherein said porous material is selected from the group consisting of polypropylene, polytetrafluoroethylene and polycarbonate.

32. A method according to claim 1, wherein said first and second liquids form a stable interface therebetween.

33. A method according to claim 32, wherein said first liquid is hydrophilic and said second liquid is hydrophobic.

34. A method according to claim 33, wherein said first liquid is selected from the group consisting of water, alcohols, and organic and inorganic acids.

35. A method according to claim 34, wherein said second liquid is a hydrocarbon.

36. An apparatus according to claim 15, wherein the size of said through pores of said porous material is from several tens of angstroms to several tens of micrometers.

37. An apparatus according to claim 36, wherein the thickness of said partition formed by said porous material is from several to several hundreds of micro-meters.

38. An apparatus according to claim 15, wherein said porous material is hydrophobic.

39. An apparatus according to claim 38, wherein said porous material is selected from the group consisting of polypropylene, polytetrafluoroetylene and polycarbonate.

40. An apparatus according to claim 15, which further comprises a three-way inlet cock having a first passage for introducing one of said first and second liquids, a second passage connected to said pressure detecting device and a third passage connected to one end of said porous material, and a two-way outlet cock having a first passage connected to the other end of said porous material and a second passage for removing one of said first and second liquids, thereby facilitating the exchange of liquid.

41. An apparatus according to claim 15, which further comprises a vessel having an inlet and an outlet, formed around said porous material for receiving the other of said first and second liquids.

* * * * *